US012193455B2

(12) United States Patent
Galet et al.

(10) Patent No.: US 12,193,455 B2
(45) Date of Patent: Jan. 14, 2025

(54) SUNFLOWER SEED PROTEIN ISOLATE AND A PROCESS FOR PRODUCING THE SAME

(71) Applicants: Avril, Paris (FR); Universite De Lorraine, Nancy (FR); Centre National de La Recherche Scientifique, Paris (FR)

(72) Inventors: Olivier Galet, Trégueux (FR); Romain Kapel, Saint Max (FR); Sara Albe Slabi, Zabrze (PL)

(73) Assignees: Avril, Paris (FR); Universite De Lorraine, Nancy (FR); Centre National de La Recherche Scientifique, Paris (FR)

( * ) Notice: Subject to any disclaimer, the term of this patent is extended or adjusted under 35 U.S.C. 154(b) by 728 days.

(21) Appl. No.: 17/416,269

(22) PCT Filed: Dec. 20, 2019

(86) PCT No.: PCT/EP2019/086810
§ 371 (c)(1),
(2) Date: Jun. 18, 2021

(87) PCT Pub. No.: WO2020/128051
PCT Pub. Date: Jun. 25, 2020

(65) Prior Publication Data
US 2022/0053791 A1 Feb. 24, 2022

(30) Foreign Application Priority Data
Dec. 20, 2018 (EP) .................................... 18306781

(51) Int. Cl.
*A23J 1/14* (2006.01)
*A23L 33/185* (2016.01)
(Continued)

(52) U.S. Cl.
CPC ............... *A23J 1/14* (2013.01); *A23L 33/185* (2016.08); *B01D 61/145* (2013.01);
(Continued)

(58) Field of Classification Search
CPC ........ A23J 1/14; A23L 33/185; B01D 61/149; B01D 61/145; B01D 61/147; B01D 61/16;
(Continued)

(56) References Cited

U.S. PATENT DOCUMENTS 6,905,713 B2  6/2005  Diosady et al.
8,728,542 B2  5/2014  Pickardt et al.

FOREIGN PATENT DOCUMENTS

CA  2751914 A1  9/2010
JP  3416312 B2  6/2003
(Continued)

OTHER PUBLICATIONS

Gonzalez-Perez et al., Physicochemical Properties of 2S Albumins and the Corresponding Protein Isolate from Sunflower (*Helianthus annuus*); C98 Journal of Food Science—vol. 70, Nr. 1 (Year: 2005).*

(Continued)

*Primary Examiner* — Brent T O'Hern
(74) *Attorney, Agent, or Firm* — ArentFox Schiff LLP

(57) ABSTRACT

A process for preparing a sunflower seed protein isolate and a protein isolate which is obtainable by such process. The process comprises the following steps: mixing a defatted seed meal with an aqueous NaCl solution at a basic pH; separating said solubilised protein solution from solids; diafiltering said solubilised protein solution through an ultrafiltration membrane system using an aqueous NaCl diafiltration NaCl solution and at least 2 diavolumes of said aqueous NaCl diafiltration solution, diafiltering said NaCl-diafiltered protein; concentrating said purified protein solution; and drying said purified protein concentrate to obtain a protein isolate.

12 Claims, 4 Drawing Sheets

(51) Int. Cl.
    *B01D 61/14*     (2006.01)
    *B01D 61/16*     (2006.01)
    *C07K 14/415*     (2006.01)

(52) U.S. Cl.
    CPC ......... *B01D 61/147* (2013.01); *B01D 61/149* (2022.08); *B01D 61/16* (2013.01); *C07K 14/415* (2013.01); *A23V 2002/00* (2013.01); *B01D 2311/10* (2013.01); *B01D 2311/18* (2013.01); *B01D 2315/16* (2013.01)

(58) Field of Classification Search
    CPC ............ B01D 2311/10; B01D 2311/18; B01D 2315/16; C07K 14/415; A23V 2002/00
    USPC ........................................................ 426/656
    See application file for complete search history.

(56) References Cited

FOREIGN PATENT DOCUMENTS

| WO | 2005107492 A1 | 11/2005 |
|---|---|---|
| WO | 2009149551 A1 | 12/2009 |

OTHER PUBLICATIONS

S Gonzales-Perez, "Physicochemical Properties of 2S Albumins and the Corresponding Protein Isolate from Sunflower (*Helianthus annuus*)", Journal of Food Science, vol. 70, Jan. 1, 2005 (Jan. 1, 2005), pp. 98-103.

Parrado J et al., "Characterization of enzymic sunflower protein hydrolyzates", Journal of Agricultural and Food Chemistry, American Chemical Society, Books and Journals Division, US, vol. 41, Jan. 1, 1993 (Jan. 1, 1993), pp. 1821-1825.

Kroll J et al., "Preparation of Rapeseed Proteins by Extraction, Ultrafiltration and Diafiltration", FETT—Lipid. Fat Scince Technology, Wiley-VCH Verlag, Weinheim, DE, vol. 93, No. 2, Feb. 1, 1991 (Feb. 1, 1991), pp. 61-65.

Mohammed Saeed et al., "Chlorogenic acid interactions with sunflower proteins", Journal of Agricultural and Food Chemistry, American Chemical Society, Books and Journals Division, US, vol. 37, No. 5, Jan. 1, 1989 (Jan. 1, 1989) pp. 1270-1274.

International Search Report and Written Opinion of the International Search Authority issued in PCT/EP2019/086810, dated Mar. 25, 2020, pp. 1-14.

European Search Report and Written Opinion of Application No. 18306781.8, dated Jun. 26, 2019, pp. 1-12.

* cited by examiner

SUNFLOWER SEED PROTEIN ISOLATE AND A PROCESS FOR PRODUCING THE SAME

CROSS REFERENCE TO RELATED APPLICATIONS

This application is a National Stage Entry of PCT/EP2019/086810, filed Dec. 20, 2019, which claims priority to EP application Ser. No. 18/306,781.8, filed Dec. 20, 2018, the disclosures of each of which are hereby incorporated by reference in their entireties.

TECHNICAL FIELD

The invention relates to a sunflower seed protein isolate and a method for its extraction.

PRIOR ART

Oil seeds, such as sunflower seeds, are an important source of proteins having a high nutritional value. In particular, proteins contained in sunflower seeds are now widely used in the food industry as, for example, food additives or stabilisers, or as major nutritious components.

Sunflower proteins are extracted as concentrates or isolates depending upon their degree of purity. Isolates must further meet a number of varied demands from the food industry in terms of solubility, exclusion of components seen as undesirable, such as phytic acid, and organoleptic properties and, in particular, colour. These characteristics are linked, at least partially, to the processes used for their extraction. Extractions are usually carried out from oilseed meals in water at a basic pH and are followed by precipitation of the proteins at an acid pH.

A great number of processes and methods are disclosed. For example:

U.S. Pat. No. 3,622,556 (1971), O'Connor, teaches that it is known to carry out an extraction step of a sunflower seed meal at a pH ranging from 9 to 11 and advantageously in the presence of neutral salt (sodium sulphite). The extracted proteins are then precipitated by lowering the pH to a range of 3.25 to 6. O'Connor describes to use a nitrogen gas blanket in order to obtain a light-colored protein isolate and to use ultrafiltration before a precipitation step of the proteins at a pH of 4.5.

U.S. Pat. No. 3,993,636 (1976), in the name of INRA, describes the extraction of proteins from sunflower seed meals at a pH ranging from 8 to 12 and advantageously the addition of a neutral salt (sodium sulphite). The liquid extract phase is then ultrafiltrated to obtained a protein isolate (≥93% (=15×6.25)).

U.S. Pat. No. 4,435,319 (1983), Pearce, teaches to wash sunflower seed meals at low pH (i.e. from 4 to 7) by addition of an acid (HCl) before extracting at low pH (<4). Pearce further teaches that unacceptable colors are also produced as a result of complexing metal ions with polyphenols such as chlorogenic acid. Once extracted, the proteins can be purified by ultrafiltration.

ORDONEZ et al. 'Obtaining a protein concentrate from integral defatted sunflower flour', Bioresource Technology 78 (2001) 187-190, describe a protein-rich concentrate (71% in dry matter) obtained by extraction of a sunflower seed meal at a pH of 10.5 in the presence of a sodium bisulfite salt at 20, 40 and 60° C. The liquid extract phase is then precipitated by lowering the pH to 4.5 using $H_3PO_4$ (0.5 mol·$L^{-1}$).

SHCHEKOLDINA et al. 'Production of low chlorogenic and caffeic acid containing sunflower meal protein isolate and its use in functional bread making' J. Food Sci. Technol. (October 2014) 51 (10): 2331-2343, describes how a sunflower meal protein isolate (SMPI) is obtained. The proteins are extracted from the meal using NaCl (10 wt %), ratio 1:8, T=45 to 55° C. for 30 min, at various pH, and then the proteins are precipitated using succinic acid. It also teaches that sunflower protein have been extracted using NaCl (1.3 mol·$L^{-1}$) at pH 6.

PICKARDT et al., 'Pilot plant preparation of light-coloured protein isolates from de-oiled sunflower (Helianthus annuus L.) press cake by mild-acidic protein extraction and polyphenol adsorption', Food Hydrocolloids 44 (2015) 208-219, describes an extraction at pH 6.4 of cold pressed cakes of sunflower seed to obtain a light coloured protein isolates. Once the extraction step has taken place an ion exchange-resin is used to remove phenolic compounds, once sufficient removal has taken place, proteins isolates are obtained by precipitation at low pH (3.2 to 3.5) by using HCl (3 mol·$L^{-1}$).

GONZALEZ-PEREZ et al. 2005 'Physicochemical properties of 2S albumins and the corresponding protein isolate from sunflower (Helianthus annuus)' in JFS C: Food Chemistry and toxicology Vol. 70, Nr. 1, 2005 describes sunflower seed isolates and sunflower seed albumins. Unlike the albumins, at an ionic strength of 30 mM of NaCl the sunflower seed protein isolate has a low solubility at pH 7, which is not above 60%. As comparative data in Example 4 below shows the isolate of the invention and the one disclosed in this 2005 publication are quite different. GONZALEZ-PEREZ teaches to use organic solvents to first extract phenolic compounds (e.g. chlorogenic acid) before extracting the proteins at a basic pH.

PARRADO J et al.: "Characterization Of Enzymatic Sunflower Protein Hydrolysates", Journal Of Agricultural And Food Chemistry, American Chemical Society, Books And Journals Division, US, Vol. 41, 1 Jan. 1993, pages 1821-1825, relates to an hydrolysate of sunflower proteins and not to native proteins.

KROLL et al "Preparation Of Rapeseed Proteins By Extraction, Ultrafiltration and Diafiltration" FETT-Lipid. Fat Science Technology, Wiley-VCH Verlag, Weinheim, DE, Vol. 93, No 2, 1 Feb. 1991, pages 61-65, describes method of obtaining rapeseed proteins. Rapeseed do not contain chlorogenic acid and consequently KROLL et al is silent on the means to extract and purify this component from a sunflower seed protein isolate.

It is therefore highly desirable to provide a high yield process to obtain a sunflower seed isolate which process is also environmentally friendly.

Alternatively or additionally it is also highly desirable to provide a sunflower seed protein isolate with negligible or at least small amounts of chlorogenic acid and/or phytic acid.

Alternatively or additionally it is also highly desirable to provide a sunflower seed protein isolate having high solubilisation properties in water and/or improved organoleptic properties.

DESCRIPTION OF THE INVENTION

It is one of the objects of the invention to provide a high yield process of low environmental impact for the production of sunflower seed protein isolates. In particular it was found that the combination of method steps which include, inter alia, a neutral protein extraction step with the use of little NaCl, or even no added salts, and a diafiltration step using a NaCl solution of low NaCl concentration is useful to achieve such a goal. More particularly the invention relates to a process for preparing a protein isolate, said protein being a sunflower seed protein, said process comprising the following steps:

(a) providing an at least partially defatted seed meal, said seed meal being a sunflower seed meal;
(b) mixing said at least partially defatted seed meal with an aqueous NaCl solution at a PH neutral or slightly acid or basic (i.e. of about 6 to 8), in order to solubilize proteins present in said at least partially defatted seed meal and to thus obtain a solubilised protein solution, wherein said aqueous NaCl solution has a NaCl concentration ranging from 0 to 1.2 mol·L$^{-1}$;
(c) separating said solubilised protein solution from solids therein;
(d) diafiltering said solubilised protein solution through an ultrafiltration membrane system having a molecular weight cutoff of about 1 to 100 kDa, said diafiltration step being effected or performed using:
an aqueous NaCl diafiltration solution having a NaCl concentration ranging from about 0.1 to 0.6 mol·L$^{-1}$; and
at least 2 diavolumes of said aqueous NaCl diafiltration solution, to obtain a NaCl-diafiltered protein solution;
(e) subsequently to step (d), diafiltering said NaCl-diafiltered protein solution through an ultrafiltration membrane system with a molecular weight cutoff of 1 to 100 kDa, said diafiltration step (e) being effected using water, to obtain a purified protein solution;
(f) concentrating said purified protein solution to obtain a purified protein concentrate; and
(g) drying said purified protein concentrate to obtain said protein isolate.

Advantageously, said process does not contain a step of precipitation of said protein after step (b) and prior to step (d). Previous methods of protein extraction often include a step wherein the solubilized proteins to be isolated are precipitated at an acid pH to a solid state before membrane filtration steps are carried out. The method of the invention preferably dispenses of such a step.

Starting Material

A sunflower seed is generally an oil seed obtained from a plant of the genus *Helianthus* and more particularly from the species *Helianthus annuus* L. and from any particular sub-species or variety of said species, including wild perennial, hybrids thereof together with mutant and genetically modified varieties.

The protein isolate according to the invention is usually obtained from a sunflower seed meal which has been, firstly, at least partially, dehulled, and, secondly, at least partially de-oiled/defatted. According to a preferred embodiment of the invention, the oilseeds are first dehulled (decorticated), at least partially (e.g. 80% wt % measured as raw material depletion), before being transformed into an oilseed meal. The use of dehulled seed has shown to be particularly effective to extract a high level of proteins.

Step a)

In the context of the invention the term 'de-oiled'/'defatted' relates to sunflower seed meals which have been ground and crushed to form a meal. Sunflower oil is partially extracted from the sunflower meal to form what is known in the art as a 'pressed cake' or a 'partially defatted/deoiled meal'. Then solvents can be used to obtain a 'defatted/deoiled cake'. Hydrophobic solvents such as pentane, and in particular hexane are the one most commonly used to remove or reduce residual oil from the pressed cake, although components such as iodotrifluoromethane (ITFM) and R134a (1,1,1,2-tetrafluoroethane) have also been disclosed. When organic solvents are used, the oil, or lipids, content remaining in the 'defatted cake' is residual (e.g. ranging from 0.1 to 4 wt % by total weight).

The meal is preferably ground into particulates and sieved so that only the fraction of particulates smaller than 500 µm is used. Meals made of fractions smaller than 700 µm, or than 800 µm or less, and even smaller than 1 mm may also be considered in order to carry out the process of the invention.

Although, as shown in the examples, any of these meals may be used, it is preferred to use a cold pressed meal which is only partially defatted. By 'cold pressed' it is particularly meant that the sunflower seed meal has been cold-pressed at a temperature of 85° C. or less, more preferably 60° C. or less. The oil, or lipids, content of a cold-pressed meal thus can be ranging from about 13 wt % to about 22 wt % of lipids (e.g. about 15%), by total weight of the cold pressed meal.

A sunflower meal after being pressed usually contains dry matter in a proportion ranging from 80 wt % to 98 wt %. The dry matter content may depend to some extend upon the method used for oil extraction. Usually a cold pressed defatted meal will have a dry matter content of 85 to 92 wt % (e.g. around 89 wt %). When an organic solvent is used the dry matter content usually increases and may range from 88 wt % to 96 wt % (e.g. around 91 wt %). The pressed, or defatted meal, may comprise from about 15 wt % to about 50 wt % of proteins, preferably from 28 wt % to 45 wt % and more preferably from 34% to 44 wt % by total weight of the dry matter content of the pressed meal. Typically, the protein content is slightly lower in a cold pressed than in a defatted cake. However the proteins obtained from a cold pressed meal are usually less denatured which can be advantageous.

The amount of phytic acid that is present in the sunflower seed meal to be used in a process according to the invention is superior to 4 wt % of the total weight of proteins of said sunflower seed meal, usually it may range from 8 to 30 wt %, for example from 10 to 30 wt %.

The amount of phenolic compounds (such as chlorogenic acid) that is present in the sunflower seed meal to be used in a process according to the invention may be usually ranging from 2 to 5 wt % in dry matter.

According to an embodiment of the invention the oilseed meal is a pressed cake or a defatted cake The invention also encompasses the use of an oilseed meal which has been processed in order to extract other substances than its oil/lipids. For example a sunflower seed meal from which some proteins have already been extracted can be used according to a process of the invention.

Step b)

The at least partially defatted sunflower seed meal is mixed with an aqueous solution in order to solubilise the proteins present in the meal. This aqueous solution is a liquid able to extract water-soluble proteins and which is mainly or essentially constituted of water, that is which at least comprises 80 wt % of water by total weight of the aqueous solution. Advantageously the aqueous solution consists, or consists essentially of water. Here the term 'water' relates to any type of available water, such as tap water or a drinking water. It may include a small proportion (e.g. less than 20 wt %, 15 wt %, 10 wt %, 5 wt %, 2 wt % or 1 wt % by total weight of liquid) of at least one another component. Such another component can be naturally occurring in the water (such as various types of salts, metallic or otherwise such as KCl, $CaCl_2$)) or added on purpose, in particular to adjust the pH and/or the ionic strength of the solution.

According to a particular embodiment of the invention the aqueous solution comprises NaCl. Hence the aqueous solution has a NaCl concentration ranging from 0 to 1.2 mol·$L^{-1}$. The total concentration of NaCl in the aqueous solution is preferably inferior or equal to 1.1, 1, 0.9 or 0.5 mol·$L^{-1}$. A particularly preferred concentration range is 0.3 to 0.5 mol·$L^{-1}$. When such a concentration is used the isolate obtained shows improved solubility at low pH. According to another variant, no salt or very little salt is used and/or added and the concentration of NaCl is low, i.e. inferior or equal to 0.3, or even inferior or equal to 0.1 mol·$L^{-1}$, that is close, or equivalent, to drinking water level. Advantageously, no other salts are added and/or only NaCl is added to the water used to solubilise the proteins.

The pH of the solution which contains solubilised protein is adjusted to be neutral, that is broadly from 6 to 8 pH. It is preferred that the pH be strictly superior to 7 and strictly inferior to 8. A pH of around 7±0.5, preferably at 7±0.4 is preferred. The pH is advantageously neutral or slightly higher, e.g. 7.3. In order to adjust the pH of the solubilised protein solution of step b) a component such as an acid or a base can be added. For example, this component can be a mineral or a salt such as sodium bisulfite or an alkali, e.g. NaOH, or a weak acid, such as citric acid, ascorbic acid or phosphoric acid. The pH adjustment, if required, can be carried out by the addition of aqueous solutions of NaOH at 1.0 mol·$L^{-1}$ and/or HCl at 1.0 mol·$L^{-1}$. Alternatively no pH adjustment is made.

It is preferred not to use solvent such as methanol, propanol, iso-propanol, tetrahydrofuran, etc, in the process of the invention, in particular to remove phenolic compounds. In particular it is preferred that no methanol, and advantageously no alcohol, or even no organic solvent, is used in the aqueous solvent used in step b). However, if an non-alcoholic organic solvent (i.e. a compound with a carbon chain) is to be used, it should only be present in amount less than 20 wt %, 15 wt %, 10 wt %, 5 wt %, 2 wt % or 1 wt % so that its presence in the final product can be reduced to an acceptable or negligible amount. Alternatively mixture of aqueous alcohol (e.g. isopropanol/water) could be considered an environmentally acceptable option, even id concentrate (e.g. 70 v/v).

The ionic strength of the solubilised protein solution should be controlled and kept at a level, which is lower than 1.0 mol·$L^{-1}$ and preferably lower than 0.5 mol·$L^{-1}$.

The sunflower seed meal and the aqueous solution are mixed together using conventional method to form a slurry which contains dissolved proteins in solution, and may further contained a suspension of protein, oil and optionally fibers as well as anti-nutritional compounds. The weight ratio of the (preferably partially defatted) sunflower seed meal/aqueous solution (preferably water) usually ranges from 1:5 to 1:20 (wt %), preferably 1:6 to 1:10 (wt %) and more preferably about 1:8 (wt %) or 1:9 (wt %).

The temperature of the slurry is preferably room temperature (i.e. 20° C.) or higher. In particular it may range from 40 to 70° C., preferably from 50 to 60° C. (e.g. around 55° C.).

The extraction or solubilisation of the proteins is usually carried out by stirring or agitating the slurry formed by the sunflower seed meal and the aqueous solution for a time period ranging from 10 min to 2 h, preferably 30 to 70 min (e.g. around 45 min or around 1 h). The stirring speed can be ranging from 100 rpm to 1000 rpm, for example from 150 rpm to 900 rpm, e.g. 600±20%. The pH adjustment can be done either before and/or during stirring.

According to a preferred embodiment, the extraction (i.e. solubilisation of the proteins) step is not carried out using a blanket of inert gases. More preferably no inert gases are used in the process of the invention.

Preliminary Step: Acidic and/or Hot Aqueous Wash

It was found useful, in particular where the starting material contains a substantial amount of fat, to carry out, at least one preliminary washing step of the meal, before the extraction step, in order to remove some residual oil or some contaminates (e.g. phenolic and phytic acids as well as and other water-soluble molecules). This preliminary washing step can be carried in various manners. The first way is to carry out a wash in aqueous acidic conditions, at ambient temperature (i.e. around 20° C.) by mixing water with the sunflower seed meal while adjusting the pH to 6 or below. The pH can be lowered substantially, for example to pH 3. However a pH ranging from 4 to 6, such as 4.8 or 6 is preferred. Any acid suitable for human or animal consumption can be used. The acids described hereinabove are particularly preferred. A second way is to carry an aqueous wash under neutral conditions and/or without adjusting the pH.

In both case the wash, acidic or neutral can be carried at ambient temperature but is preferably carried out at an elevated temperature. In particular this temperature may range from 40 to 70° C., preferably from 50 to 60° C. (e.g. around 55° C.). Further, it has been found that it is advantageous to carry out more than one preliminary wash of the meal. Such a re-wash can be of the same type in respect of pH or temperature as the first preliminary wash, or different. The particular conditions of carrying out any of these preliminary washing, or re-washing, steps, such as the relative proportion of solids/liquid (S/L) to use, the mixing time, the S/L separation, etc., can advantageously be as described hereinabove in respect of step b). The pH adjustment, if carried out, can be done either before and/or during stirring.

The washed, or re-washed solids are separated from the liquid phase by conventional methods such a centrifugation and/or sieving. These solids then constitute the sunflower seed meal which is extracted as described in step b).

Step c)

Once step b) is carried out (with or without an aqueous washing step of the solids) the liquid phase containing the solubilised protein solution is separated from the slurry/solids in suspension. The means to carry out this separation are well known in the art and include centrifugation means, such as a decanter centrifuge, filtration means, pressing means, such a screw press, a filter press, a belt press, a French press, decantation means, and/or any other means that separates the slurry into a solid phase and a liquid phase. This separation may be performed using a decanter centrifuge, for example at g force ranging from 2,000 to 6,000 g, preferably from 3,000 to 5,000 g, for example about 4,600 g. As the skilled person will directly understand the solid phase contains a small proportion of liquid and conversely the liquid phase will comprise a small proportion of solids or solid particles. Hence, in a particular embodiment of the invention the liquid phase containing residual solids is further subjected to another separation step using for example a sieve or at least one disk stack centrifuge. The g-force of this centrifugation may be ranging from 6,000 to 20,000 g, optionally 17,000 g.

The spent meal can either be disregarded or recycled. The recovered liquid is then processed through diafiltration steps.

The solubilised protein solution is enriched in protein and is subjected to at least two diafiltration steps, and preferably some preliminary purification steps such as filtration, microfiltration, or ultrafiltration to recover a purified protein solution.

Optional Re-Wash Step

In an optional particular embodiment of the invention, the (sunflower) spent meal obtained from step c) described above is further subjected to a washing step. The spent meal is mixed with an aqueous solution, which consists or consists essentially of water, as described above, without pH adjustment. It is preferred not to add an acid, a base, a mineral, a salt and/or a solvent as defined above. The spent meal and the aqueous solution are mixed together using conventional method to form a slurry which contains dissolved proteins in solution, and may further contained a suspension of protein, oil and optionally fibers as well as anti-nutritional compounds. The weight ratio of the spent meal/aqueous solution (preferably water) usually ranges from 1:1.5 to 1:4 (wt %), preferably 1:1.5 to 1:2.5. The temperature of the slurry is preferably room temperature (i.e. 20° C.) or higher. In particular it may range from 40 to 70° C., preferably from 50 to 60° C. (e.g. around 55° C.). The solubilisation of the proteins is usually carried out by stirring or agitating the slurry formed by the sunflower seed meal and the aqueous solution for a short time period ranging from 2 min to 10 min, preferably 3 min to 7 min. The stirring speed can be ranging from 100 rpm to 1000 rpm, for example from 150 rpm to 900 rpm, e.g. 600±20%. The liquid phase containing the solubilised protein solution is then separated from the slurry/solids in suspension as described in step c) above. The second solubilised protein solution enriched in protein is pooled with the first solubilised protein solution enriched in protein. The pooled solution enriched in protein is then subjected to at least two diafiltration steps, and preferably some preliminary purification steps such as filtration, microfiltration, or ultrafiltration to recover a purified protein solution.

In certain embodiments, the optional re-wash step allows increasing the protein extraction yield by at least 5%, preferably at least 10% and more preferably 15%.

Step d)—NaCl Diafiltration

As mentioned above the solubilised protein solution is diafiltered with a NaCl aqueous solution. More than one diavolume of the NaCl solution are being used, preferably. The NaCl concentration of said diafiltration solution ranges from 0.1 to 0.6 mol·L$^{-1}$, but is preferably chosen in the group consisting of 0.1, 0.2, 0.3, 0.4 and 0.5 mol·L$^{-1}$. A preferred concentration range is from 0.2 or 0.5 mol·L$^{-1}$. The temperature at which this diafiltration step is carried out can be at ambient, or room, temperature or at a higher temperature. For example it can range from 10° C. to 70° C., in particular from 15° C. to 60° C., preferably around 55° C. The temperature and the NaCl concentration of the diafiltering solution appear to be linked and it is recommended to choose higher NaCl concentration for lower diafiltration temperature or vice versa.

The diafiltration system used is an ultrafiltration membrane system of the type well known in the art having a porous membrane, wherein the molecular weight cut-off (MWCO or nominal pore size) may range from 1 to 100 kDa, and preferably from 1 to 10 kDa, in particular 3 kDa. The membrane can be in the shape of flat sheet or hollow fibers membrane. Advantageously the UF membrane system has hollow fibres. The membrane surface of the UF membrane system can vary and may range from 0.05 m$^2$ to 5 m$^2$ depending upon the volume of solubilised protein solution to be purified. For industrial scale membrane surface usually range from 0.1 m$^2$ to 5 m$^2$. The membrane of the filtering device is made of a suitable material such as a polysulfone (PS) or a polyethersulfone (PES) which has high protein retention. A diavolume (DV) is a measure of the extent of washing that has been performed during a diafiltration step. It is based on the volume of diafiltration solution introduced into the unit operation compared to the retentate volume. In the process of the invention a constant-volume diafiltration is being performed. The retentate volume is held constant and the diafiltration buffer enters at the same rate that the filtrate leaves. In these conditions a diavolume is calculated as:

$$DV=[\text{Total buffer volume introduced to the operation during diafiltration}]/[\text{retentate volume}].$$

The diafiltration step seeks to remove most compounds or at least one member of the group of compounds constituted of solubilised phytic acid, phytic acid derivatives, sugars, low molar weight carbohydrates, free phenolic compounds, non-protein nitrogen, mineral compounds and mixture thereof. According to a preferred embodiment of the invention at least 4 DV are used and more advantageously 5 or more, e.g. up to 6, 7, 8, 9, 10, 11, 10, 11, 12, 13 or 14.

According to a preferred embodiment, the solubilised protein solution can be concentrated prior, and advantageously immediately prior to, the above described NaCl solution diafiltration step. The concentration can be carried out using the ultrafiltration device described above. The level of concentration chosen can be achieved applying a volumetric reduction factor (VRF=[volume of the feed]/[volume of the retentate]) of 2 to 10 of the solubilised protein solution, but is advantageously ranging from 2 to 6, and in particular to 3 to 5. Hence the concentration can be carried out by a VRF of 2, 3, 4, 5, 6, 7, 8, 9 or 10.

Preliminary Microfiltration Step

As abovementioned, a preliminary filtration step, using a microfiltration device can be carried out. Such a microfiltration may be performed by using a device having a filtration membrane (e.g. in polyamide, polysulfone (PS) or polyvinyllidene difluoride (PVDF)) having for example a nominal pore size ranging from 0.05 μm to 2 μm, preferably from 0.1 μm to 1 μm, e.g. 0.22 μm. Microfiltration may, as well, comprise a washing step using water, either cold or hot such as 40° C. to 70° C., e.g. 55° C., wherein one (or more) DV is used. In particular 2, 3 or more DV can be used. The water used for the wash can be salted, for example with NaCl. The concentration of the salt in the wash may range from 0.1 to 1 mol·L$^{-1}$, such as 0.5±0.2. As mentioned above an elevated temperature can be selected in order to decrease the salt concentration or vice versa.

According to a preferred embodiment, the solubilised protein solution can be concentrated prior to, and advantageously immediately prior to, the ultrafiltration step. The concentration can be carried using the microfiltration device described above. The level of concentration of the solubilised protein solution can be a VRF of 2 to 10 of the solubilised protein solution, but is advantageously ranging from 3 to 5, e.g. 3.5. When such a step is used, the collected permeate from this microfiltration step is the solubilised protein solution which is to be subjected to the ultrafiltration step above described.

pH Adjustment

According to an aspect of the invention the pH of the retentate of the ultrafiltration step above mentioned is advantageously increased to above 7, above 8 or above 9. Particularly the pH may be adjusted to a pH ranging from 7 to 10, preferably 8 or 9, ±20%. This adjustment can be made by the addition of a pH modifier such as NaOH, e.g. aqueous solution of NaOH and/or HCl (both at concentrations such as 1 mol·L$^{-1}$).

Furthermore it may be considered to control and/or adjust the pH for others or all the filtration and/or the diafiltration steps. In order to adjust the pH, a pH modifier as disclosed in this specification can be added, e.g. phosphoric acid, NaOH, etc. to the water. Preferably the pH is controlled for at least two and preferably all the purification steps subsequent to step d). Such a controlled pH may advantageously be as described in the previous paragraph.

Step e) Diafiltration in Water (Wash)

Once the NaCl diafiltration, and eventually the pH adjustment, is carried out, a further diafiltration step(s) is carried out on the retentate obtained from the described NaCl diafiltration step with water. The water used can be tap water but is advantageously purified by removing organic/inorganic particles and contaminants and eventually dissolved gases. The retentate is washed using preferably 1 to 10 DV of cold or hot water, preferably more than 1 DV, such as 2, 3, 4, 5, or 6 DV, or more.

Step f) Concentrating Step

This retentate is then concentrated using, for example, an UF membrane system such as the one described above. The level of concentration of this solubilised protein solution can be one of a VRF of more than 1 and up to 10 of the solubilised protein solution, but is advantageously about 2, 3 or 4.

Step g) Drying Step

In order to obtain an isolate and to preserve the structure of the sunflower protein thus isolated by the process of the invention, it is advantageous to freeze dry, lyophilized or to spray dry the purified protein solution in order to obtain a dry powder. These techniques are well known in the art. For instance, to freeze dry, the purified protein concentrate is frozen at temperature from −80° C. to −20° C. until complete freezing. Then freeze-drying is carried out by the use of a standard freeze dried apparatus at a sublimation temperature around −20° C. To spray dry, it is customary to use a standard vertical spray dryer equipped with nozzle, with an inlet temperature ranging from 150° C. to 200° C. and an outlet temperature ranging from 70 to 90° C. These methods permit to obtain a powder having less than 7 wt % of water, and preferentially less than 4 to 6 wt %.

The process of the invention further encompasses a process wherein any one of steps above described may be repeated, eventually more than once.

According to another embodiment of the invention the steps from step b) to step e) or f) are carried out at one temperature, e.g. either at ambient or at an elevated temperature such as, 40° C. to 70° C., preferably 50 to 60° C., in particular around 55° C.

It was found that the use of such an elevated temperature for any of these steps b) to e), and preferably all, to be beneficial, particularly in terms of increased solubility at neutral pH of the resulting isolate and/or of lowering even more the chlorogenic acid content.

Protein Isolate

A sunflower seed protein isolate obtainable or obtained by the process or processes described therein is a further object of the invention.

A sunflower seed isolate (SI) according to the invention preferably comprises at least the two main groups of sunflower proteins: helianthinin (sunflower globulins) and sunflower albumins (SFAs).

Advantageously the sunflower seed isolate of the invention can have an improved solubility profile in aqueous solution. By improved solubility profile it is meant the solubility may range from 90% to 100%, preferably from 95% to 100%, in either acidic pH such as pH 3, 3.5, and/or 4, and/or is ranging from 90% to 100%, preferably from 95% to 100% at neutral pH (around pH7). A preferred embodiment is an isolate which has a solubility ranging from 90% to 100%, preferably from 95% to 100%, in acidic pH such as pH 3 and 3.5, and ranging from 90% to 100%, preferably from 95 to 100%, at neutral pH (around pH7). The measure of the solubility is carried out according to the protocol described below under the section headed analytical methods.

Another object of the invention is a sunflower seed protein isolate with a solubility in aqueous solution which is superior to 65%, preferably superior to 85%, at pH 3. Advantageously said protein isolate has a solubility in aqueous solution which is superior or equal to 85% at pH 3 and/or superior or equal to 75% at pH 3.5. More advantageously said protein isolate has a solubility in aqueous solution which is superior or equal to 65% at pH 7, preferably superior or equal to 70% at pH 7, more preferably superior or equal to 75% at pH 7.

A preferred sunflower seed protein isolate has a solubility in aqueous solution which is superior or equal to 85% at pH 3 (advantageously superior or equal to 95%) and superior or equal to 75% at pH 3.5 (advantageously superior or equal to 95%) and, preferably, superior or equal to 75% at pH 7.

According to a preferred embodiment of the invention the sunflower seed protein isolate of the invention has an aqueous solubility superior, or equal, to 95% at pH 3 and/or an aqueous solubility superior, or equal, to 90% at pH 7.

As mentioned before such particular solubility profiles are advantageous as they can meet particular needs in foodstuff preparation such as solubility in acidic food (e.g. beverage). Thus a preferred isolate of the invention is an isolate having a solubility which is equal or superior to 90% (in particular equal or superior to 95%) from pH 3 to pH 3.5 and advantageously from pH 3 to pH 4. According to an advantageous aspect of the invention the isolate has a solubility which is equal or superior to 90% from pH 3 to pH 4.

At pH 3, the solubility of the isolate can be at least 95%, preferably 99%, or more.

At pH 3.5 the solubility of the isolate can be at least 95%, preferably 99%, or more.

At pH 4 the solubility of the isolate can be at least 90%, preferably 95%, or more.

This high solubility can be combined also to a high solubility (i.e. ranging from 90 to 100% (preferably superior to 95%) at a neutral pH (around 7).

Another object of the invention is a sunflower seed protein isolate with a solubility in aqueous solution at an ionic strength of 0.03 M (0.03 mol·L$^{-1}$) which may range from 90% to 100% in either acidic pH such as pH 3, 3.5, and/or 4, and/or is ranging from 80% to 96%, preferably from 90% to 98%, and even more preferably from 94 to 100% at neutral pH (around pH7). A preferred embodiment is an isolate which has a solubility ranging from 90% to 100%, preferably from 95% to 100%, in acidic pH such as pH 3 and 3.5, and, ranging from 90% to 96%, preferably from 94 to 100%, at neutral pH (around pH7).

According to another object of the invention the sunflower seed protein isolate has a solubility in aqueous solution at an ionic strength of 0.03 M (0.03 mol·L$^{-1}$) which may range from 90% to 96%, preferably from 90% to 100% and even more preferably from 94 to 100%, at neutral pH (around pH7).

According to another object of the invention the sunflower seed protein isolate has a solubility in aqueous solution at an ionic strength of 0.03 M (0.03 mol·L$^{-1}$) which may range from 90% to 100%, preferably from 95% to 100% in acidic pH and in particular at pH 3.5, and eventually pH 4, The measure of the solubility of the aqueous solution at an ionic strength of 0.03 M is advantageously carried out according to the protocol described in example 4.

Chlorogenic acid compounds are a major cause of the dark colour and undesirable taste of sunflower seed protein isolates. In sunflower seed, these compounds are mainly three isomeric forms of chlorogenic acid 3-CQA, 4-CQA and 5-CQA.

An object of the invention is a sunflower seed protein isolate which contains no or negligible amount of any or all of such compounds and a method of obtaining it. A negligible amount of a chlorogenic acid compound can be an amount equal or inferior to 1%, preferably equal or inferior to 0.5%, advantageously equal or inferior to 0.2%, using the measuring method described herein below. Hence, a further object of the invention is a sunflower seed protein isolate obtainable or obtained by the process or processes above described and/or having a content of at most 0.2% in weight (dry matter) of at least one chlorogenic acid isomer by weight of total proteins in said isolate. Preferably, the isolate has less than 0.2 wt % of all chlorogenic acids isomers, aka 'chlorogenic acid' by weight of proteins in said isolate.

Phytic acid is a component generally seen as undesirable by the food industry. Hence a further object of the invention is a sunflower seed protein isolate which contains a decreased amount, or a low amount, of phytic acid. A decreased amount of phytic acid can be a decrease of more than 85%, preferably more than 90%, advantageously more than 96% of the amount (mass) of phytic acid contained in the sunflower seed meal to be used. A low amount of phytic acid can be an amount equal or inferior to 5% (e.g. 4%), preferably equal or inferior to 2%, and advantageously equal or inferior to 1%; using the measuring method described herein below. Hence, a further object of the invention is a sunflower seed protein isolate obtainable or obtained by the processes above described and/or having at most 2 wt. % of phytic acid, preferably less than 1.8 wt. % and more preferably less than 1.5 wt %, by weight of total proteins in said isolate.

Preferably the isolate of the invention has also a purity of at least 85 wt %, preferably at least 90% (N×6.25) on a dry protein isolate.

The term 'protein' used herein is intended to cover any protein or mixture of proteins naturally occurring in sunflower seeds.

Proteins are available as hydrolysates, concentrates and isolates. Hydrolysates are proteins that have been partially broken down and unfolded by exposing them to heat, acid or enzymes to break apart some bonds linking amino acids and make them more digestible. Many protein extracts are concentrates which have a content of around 80% by total weight of dry matter.

The sunflower seed protein isolate of the invention is preferably a native protein (e.g. not hydrolysed and/or non-denatured) and usually is a particulate state, such as a powder. The protein isolate of the invention has a protein content of at least 90 wt %, usually at least 95 wt % and usually more advantageously more than 97 wt % by total weight of the solid isolate. Proteins content is measured on dry matter content by determining the nitrogen content using the Kjeldahl method (see infra) and multiplying it by a standard conversion factor of 6.25 (i.e. N×6.25 conversion factor). Although this is a widely accepted measurement in the art its does include some uncertainty. Hence protein contents of above and over 100% can be measured. However as this is the standard measure in the art, this is the measure which will be adopted to define the expression "protein content" within the meaning of the invention. The isolate of the invention is advantageously a powder which comprises at least 90% (wt %) of dry matter.

Preferably the isolate has also a purity of at least 90 wt %, preferably at least 95% (N×6.25) on a dry protein isolate.

The sunflower seed protein isolate comprises native proteins which are mostly globulins and albumins. It is preferred that the sunflower protein isolate of the invention comprises from 60 wt % to 80 wt % of globulins and from 20 wt % to 40 wt % of albumins, in percentage relative to the total mass of these two types of proteins. Preferably these mass percentages range from 63 mass % to 73 wt % (globulins) and from 21 mass % to 37 mass % (albumin).

An isolate which has about 76.5±2.50 mass % of globulins and/or about 23.5±2.30 wt % of albumins is a particularly preferred object of the invention.

An isolate which has about 71.80±0.93 mass % of globulins and/or about 28.20±0.93 mass % of albumins is a particularly preferred object of the invention. An isolate which has about 64.44±0.70 mass % of globulins and/or about 35.56±0.70 wt % of albumins is a particularly preferred object of the invention.

According to a preferred embodiment the protein isolate of the invention has a light colour, such as beige, light brown or greenish. The colour of the isolate is preferably defined by the coordinates L* (lightness), a* and b*, wherein the a* axis represents the green-red component, with green in the negative direction and red in the positive direction and wherein the b* axis represents the blue-yellow component, with blue in the negative direction and yellow in the positive direction. These coordinates are measured by the method described in the Examples. Hence the isolate can advantageously be defined as having the following coordinates:

$$L^* = 84.32 \pm 3.71,$$

$$a^* = 1.08 \pm 1.45 \text{ and}$$

$$b^* = 34.78 \pm 2.66.$$

Preferably ΔE=50 or less, and by order of increasing preference, 40 or less, 30 or less, 20 or less, 15 or less, 10 or less, 8 or less, 7 or less, 5 or less.

The scope of the invention also extends to the use of the isolate of the invention as described therein in the food industry, for example as a main component, a supplement or an additive. Hence the isolate can be used according to the invention in food product or food ingredient, preferably for beverages, such as acidic beverage with a pH value less than 5, preferably less than 3.5. A drink with at least 1% protein content, coffee and chocolate preparation including a whitener or not, soft drinks, are also part of the invention. A food or drink containing such isolate is a further object of this invention as well as the method of making a foodstuff, or a food supplement, by adding and/or mixing said isolate to other ingredients.

EXAMPLES

Figure 1:
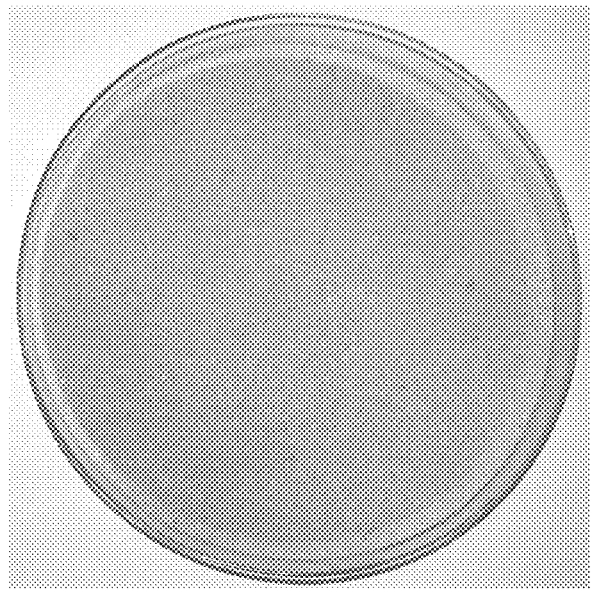
FIG. 1 is a view of a Petri dish containing a sunflower seed protein isolate according to example 1.

Description of Analytical Methods
Dry Matter Content

Approximately 250 mg of protein powder is weighted on a dried aluminium disk and the exact mass is recorded and placed in a drying oven set at 110° C. After a minimum of 24 h, the sample is let to cool to ambient temperature in a desiccator and reweighted. The dry matter content in the sample is calculated according the formula (Equation 1).

$$DM(\%) = \frac{m_d}{m_w} \times 100 \quad \text{(Equation 1)}$$

wherein:
DM—dry matter content (%),
$m_d$—mass of powder after drying (mg),
$m_w$—mass of powder before drying (mg).

Kjeldahl Method Used for Protein Content Determination

The Kjeldahl method is used for the determination of the protein content in liquid samples (to assess the solubility of isolates) or in solid samples to determine their protein contents and is described for example in the standard NF EN ISO 5983—2 Oct. 2009.

1. Preparation of an Isolate Sample Powder

A 0.5 to 2 mL sample is taken into a Kjeldahl flask. The exact volume is recorded.

2. Preparation of a Solid Sample (Meal)

Weigh between 20 and 40 mg of meal in a Kjeldahl Weighing Boat N-free provided by Büchi. Record the exact weight.

Put the boat and the sample in a Kjeldahl flask.

3. General Procedure

In the Kjeldahl flask, introduce 4 mL of sulfuric acid at 96% (v/v) and approximately 0.2 g of catalyst Cu—Se from AppliChem Panreac (Gatersleben, Germany).

As control, at least one flask is prepared with no sample but with sulfuric acid and catalyst.

Then, the mineralization step is carried out in several steps in a Büchi SpeedDigester K-439 (Rungis, France):
Preheating to 150° C.
Heating for 15 min at 150° C.
Heating for 90 min at 450° C.

These steps are done to decompose organic substances: in particular, nitrogen is reduced as $NH_4^+$.

The samples are allowed to cool down for 30 min.

The next step is the distillation: sodium hydroxide 32% is added to the sample to convert nitrogen to its $NH_3$ form which is distilled, then converted back to $NH_4^+$ with 3% boric acid (w/v) and then back titrated with 0.01 mol·L$^{-1}$ HCl and 3% boric acid in a Kjelflex K-360 from Buchi associated with a Titrino Plus 877 from Metrohm (Herisau, Suisse). The equivalent volume is used in the following calculation.

4. Calculation of the Protein Content

Hence, the total nitrogen content (NTK in g·L$^{-1}$) is determined according to the following formula:

$$NTK = \frac{(V_{assay} - V_{blank}) \times M(N) \times C_n(\text{HCl})}{V_{sample}} \quad (1)$$

$V_{assay}$ and $V_{blank}$ are the volumes of HCl at a concentration of Cn (HCl) equal to 0.01 mol·L$^{-1}$ (in mL) used for the back titration. The molecular mass of nitrogen is 14 g·mol$^{-1}$, and $V_{sample}$ is the volume of extract used as sample for the analysis. For solid sample analysis, $V_{sample}$ is replaced by the mass of meal introduced in the flask (in mg) and the result becomes a rate of nitrogen in %.

The total nitrogen content is then converted into proteins thanks to a coefficient equal to 6.25.

Protein content=$NTK \times 6.25$

It is understood by the skilled person that this measure of protein content is proportional to the amount of nitrogen in the sample.

The standard factor, 6.25, to convert nitrogen to protein content was used. However, the value of this factor may differ for sunflower proteins. Consequently, the purity of powder may exceed 100% in some cases.

Purity of Protein Powder

Exactly 125 mg of protein powder is weighted, the exact mass recorded, and then dissolved in a beaker in 5 mL of a NaOH solution (0.1 mol·L$^{-1}$). The solution is transferred into a 25 mL volumetric flask at room temperature. The beaker is washed three times with 5 mL of a NaOH solution (0.1 mol·L$^{-1}$) and the washing solutions are transferred into a 25 mL volumetric flask. Finally, the volumetric flask is completed with the same NaOH solution. Final volume of the mixture was 25 mL. The concentration of proteins in the solution was measured according the Kjeldahl method (see below). The purity of protein in powder on dry matter base was calculated as follows (Equation 2).

$$\text{Protein}/DM_{DM}(\%) = \left(\frac{C_{prot}}{C_{pow} \times \frac{DM}{100}}\right) \times 100 \quad \text{(Equation 2)}$$

wherein:

Protein/DM—purity of protein powder on dry matter base (%), $C_{prot}$—concentration of proteins in prepared solution according the Kjeldahl method (g·L$^{-1}$), $C_{pow}$—concentration of powder in prepared solution (g·L$^{-1}$), DM—dry matter content of powder (%).

Protein Solubility at Room Temperature

The solubility of the protein isolate of the invention in aqueous solution is measured as follows:

In a non-controlled condition of temperature (about 20° C.), about 500 mg of protein powder is weighted, the exact mass recorded, and then dissolved in 50 mL of a distilled water in a beaker. The solution is transferred into a 100 ml volumetric flask at room temperature. The beaker is washed three times with 10 mL of distilled and the washing solutions are transferred into a 100 mL volumetric flask. Finally, the volumetric flask is completed with distilled water. A volume of 20 mL of solution is placed in a 25 ml beaker and stirred on a stirring plate at approximatively 300 rpm at room temperature during 10 min. Then, the pH of the solution is adjusted to the required pH using an aqueous solution of 0.1 mol·L$^{-1}$ NaOH or 0.1 mol·L$^{-1}$ HCl and the stirring maintained during 30 min. After this time, the solid precipitate was separated by centrifugation at 15000 g during 20 min at 20° C. Subsequently, the concentration of protein in the initial solution and in the supernatant was measured according the Kjeldahl method (N×6.25). The protein solubility at the given pH was calculated as follows (Equation 3).

$$Sol_{pH} = \left(\frac{C_s \times V_s}{C_i \times V_i}\right) \times 100 \quad \text{(Equation 3)}$$

wherein:

$Sol_{pH}$—protein solubility at given pH (%), $C_s$—protein concentration in supernatant (g·L$^{-1}$), $V_s$—final volume of solution after adjustment of pH (mL), $C_i$—initial protein concentration (g·L$^{-1}$), $V_i$—initial volume of solution (mL).

For comparison purposes, solubility at a particular ionic strength (0.03 mol·L$^{-1}$) was also measured according to the modus operandi recited in example 4.

Phytic Acid Content

The method to determine the percentage of phytic acid in a protein extract or isolate was adapted from García-Estepa et al. (1999, Food International Research) and is applied directly to solid samples such as protein isolates and meals. For each batch of analysis, a "blank" measurement is carried out with all the reactants excepting the sample to be measured. This method consists of four stages-extraction, reaction, recovery of Fe$^{3+}$ ions and titration.

1. Extraction:

A quantity of about 250 to 500 mg of protein isolate or sunflower meal is weighted, its exact weight recorded, and then placed in a 25 ml beaker. A volume of 20 mL of a solution of 0.4 mol·L$^{-1}$ HCl+10% Na$_2$SO$_4$ (w/v) is added and the mixture is stirred at approximatively 300 rpm for minimum 120 min at room temperature. After this time, the mixture is centrifuged at 10000 g during 30 min at 20° C. and supernatant was additionally filtered (0.22 μm). The blank assay consisted of a sample containing no protein.

2. Reaction:

In a 15 mL centrifuge tube a reaction mixture composed of 2.5 mL of 20 mmol·L$^{-1}$ FeCl$_3$, 2.5 mL of 0.4 mol·L$^{-1}$ HCl+10% Na$_2$SO$_4$ (w/v) and 2.5 mL of 20% sulfosalicylic acid (w/v) is prepared. 2.5 mL of filtered sample is added to the mixture and the tube is shaken for approximatively 3 min. The color formed should be burgundy. The centrifuge tube is plunged in a 100° C. water bath for 15 to 20 min. During this step a precipitate is formed between sulfosalicylic acid, Fe$^{3+}$ ions and phytic acid. The sample is then cooled to ambient temperature and subsequently centrifuged at 10000 g during 30 min at 20° C. The supernatant is recovered.

3. Recovery of Fe$^{3+}$ Ions:

The following steps are useful to recover the maximum free ions Fe$^{3+}$:

The supernatant is filtered on a 0.22 μm filter in a 25 mL volumetric flask.

A volume of 4 mL of distilled water is added to the tubes containing the precipitates.

The tubes are stirred vigorously to put the precipitate in suspension. A vortex can be used.

The samples are centrifuged for 10 min at 10000 g.

The above steps with an asterisk "*" are repeated in the same order three times for each sample. Water is added to obtain a 25 mL solution for each sample.

4. Dosage of Free Ions Fe$^{3+}$:

A volume of 10 mL of the previous solution and 10 mL of distilled water is placed into a 25 ml beaker. The pH of mixture is adjusted to 2.5±0.5 using glycine powder (purity of at least 99%). The mixture is then heated 30 min in a water bath to a temperature ranging from 70 and 80° C. The dosage is carried out directly after the water bath, by addition of drops of an Ethylene diamine tetra acetic acid (EDTA) solution (2 mmol·L$^{-1}$) placed in a burette beforehand.

The equivalent volume is reached when the solution changes color from a burgundy color to yellow-green.

The equivalent volume is recorded as precisely as possible.

Calculations:

The EDTA dosage allows the quantification of free Fe$^{3+}$ ions in the medium. These free Fe$^{3+}$ ions are the ones which have not precipitated with the phytic acid present in the solution.

$$n(Fe^{3+})_{free} = V_{eq} \times C_{EDTA} \times \frac{V_{sol}}{V_s}$$

wherein:

$C_{EDTA}$—concentration of EDTA (mmol·L$^{-1}$), $V_{eq}$—equivalent volume (L), $V_{sol}$—volume of initial solution (L), $V_s$—volume of taken sample from initial solution (L).

The total amount of Fe$^{3+}$ introduced in the medium is obtained with the dosage of a blank, that is to say, a solution which contains no sample but has been processed as described above. The following formula gives the amount of Fe$^{3+}$ in the precipitate.

$$n(Fe^{3+})_{precipitate} = n(Fe^{3+})_{total} - n(Fe^{3+})_{free}$$

This formula can also be written as:

$$n(Fe^{5+})_{precipitate} = n(Fe^{3+})_{blank} - n(Fe^{3+})_{free\ in\ the\ sample}$$

In the literature, it is usually admitted that 6 phosphorus bind to 4 ions $Fe^{3+}$ $$\frac{n(\text{Phosphorus})}{n(Fe^{3+})} = \frac{6}{4}$$

However, if one molecule of phytic acid contains 6 phosphorus, $$n(\text{Phytic Acid}) = \frac{n(\text{Phosphorus})}{6}$$

then the combination of the last two formulae is:

$$n(\text{Phytic Acid})_{precipitate} = \frac{n(Fe^{3+})_{precipitate}}{4}$$

As 2.5 mL are taken from the initial volume of 20 mL, the molar concentration of phytic acid in the extract is 8 times the concentration of $Fe^{3+}$ ions in the precipitate.

$$n(\text{Phytic Acid})_{extract} = 8 \times n(\text{Phytic Acid})_{precipitate}$$

The mass of phytic acid in the extract is:

$$m(\text{Phytic Acid})_{extract} = n(\text{Phytic Acid}) \times M(\text{Phytic Acid})$$

M(Phytic Acid) corresponds to the molecular weight of phytic acid, which is equal to 660 g·mol$^{-1}$ under the IP6 form.

The phytic acid content is usually expressed in mg·g$^{-1}$ of protein or in mg·g$^{-1}$ of dry matter corresponding to:

$$\text{Phytic acid content in mg·g}^{-1} \text{ of protein} = \frac{m(\text{Phytic Acid})_{extract}}{m(\text{Protein})_{extract}}$$

$$\text{Phytic acid content in mg·g}^{-1} \text{ of dry matter} = \frac{m(\text{Phytic Acid})_{extract}}{m(\text{Dry matter})_{extract}}$$

Chlorogenic Acid Content

Chlorogenic acid is an ester of caffeic and quinic acid and occurs in sunflower seeds mainly as three isomers: 3-caffeoylquinic acid (3-CQA), 4-caffeoylquinic acid (4-CQA) and 5-caffeoylquinic acid (5-CQA).

Figure 5:
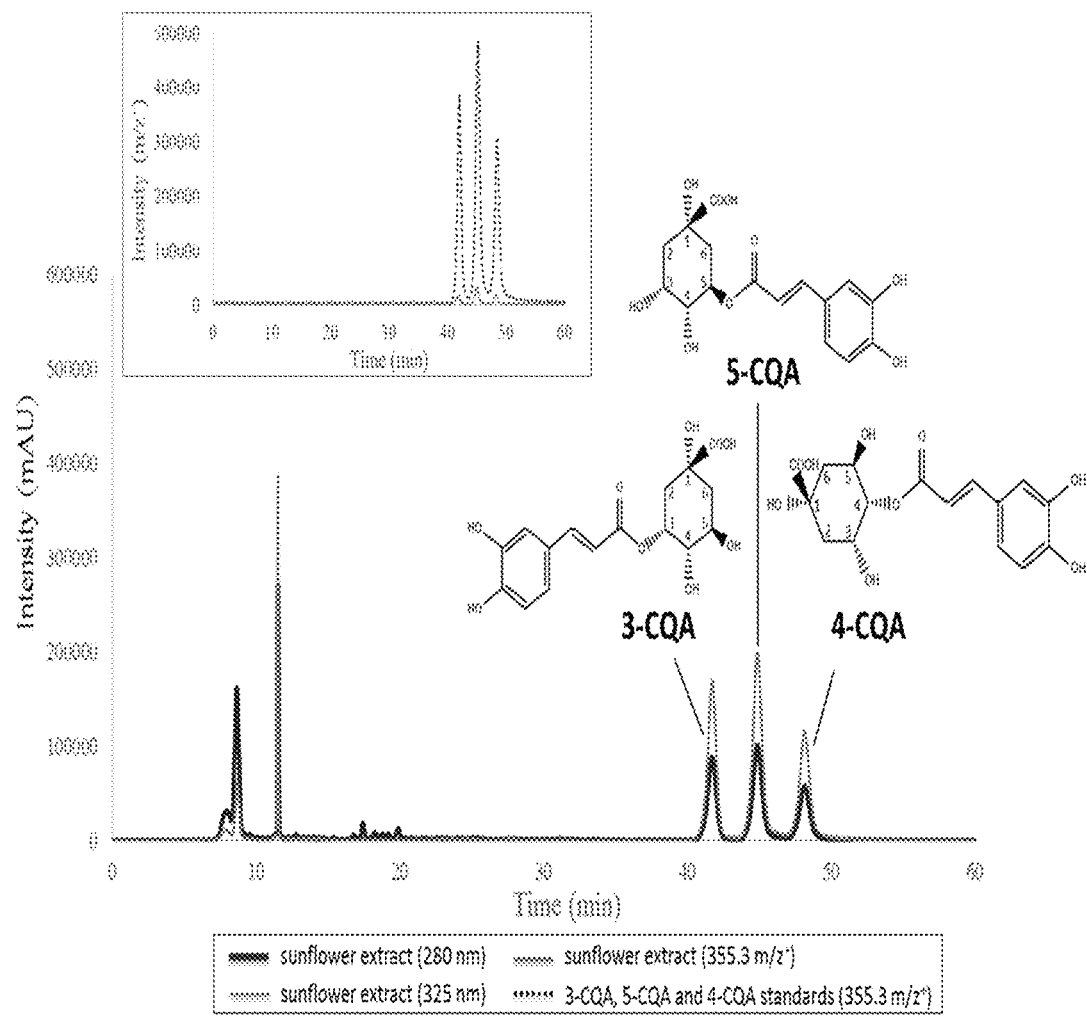
FIG. 5 is a graph representing the size exclusion chromatogram of sunflower meal extract (red bold line-detection 280 nm, green thin line-detection 325 nm). The X-axis represents time in minutes. The Y-axis represents intensity in milli absorption units. The internal, boxed, figure represents the mass spectrum at m/z 355.3$^+$ of sunflower extract (orange continuous line) and reference substances of chlorogenic acid isomers (black dotted line): 3-caffeyolquinic acid (3-CQA), 5-caffeyolquinic acid (5-CQA) and 4-caffeyolquinic acid (4-CQA).

For quantification of their respective contents in a particular sample a method by Size Exclusion Chromatography (SEC) is chosen. This method was validated according to the ICH Guidelines, 'Validation of analytical procedures: text and methodology Q2R1', November 2005). For this purpose, about 25 mg of protein powder is weighted, the exact mass recorded, and then dissolved in a beaker in 1 mL of a buffer (Tris-HCl 0.25 mol·L$^{-1}$/NaCl 0.5 mol·L$^{-1}$, pH 7.0). The solution is transferred into a 5 mL volumetric flask at room temperature. The beaker is washed three times with 1 mL of a buffer (Tris-HCl 0.25 mol·L$^{-1}$/NaCl 0.5 mol·L$^{-1}$, pH 7) and the washing solutions are transferred into the 5 mL volumetric flask. Finally, the volumetric flask is completed with the same buffer (Tris-HCl 0.25 mol·L$^{-1}$/NaCl 0.5 mol·L$^{-1}$, pH 7). Subsequently, 5 µL of said solution is injected into Biosep SEC-s-2000 column (300×7.5 mm; 5 µm) which is maintained at 35° C. The mobile phase used consists of acetonitrile/0.1% formic acid (10:90 v/v) and the flow rate is set on 0.6 mL·min$^{-1}$. The retention times of chlorogenic acid isomers based of an aqueous extract of sunflower meal are confirmed after injection of 3-, 4- and 5-CQA standard solutions. These measures (see FIG. 5) are conducted using a quadrupole mass spectroscopy detector (m/z 355.3$^+$) and a diode array detector at 325 nm of analytical wavelength.

Figure 6:
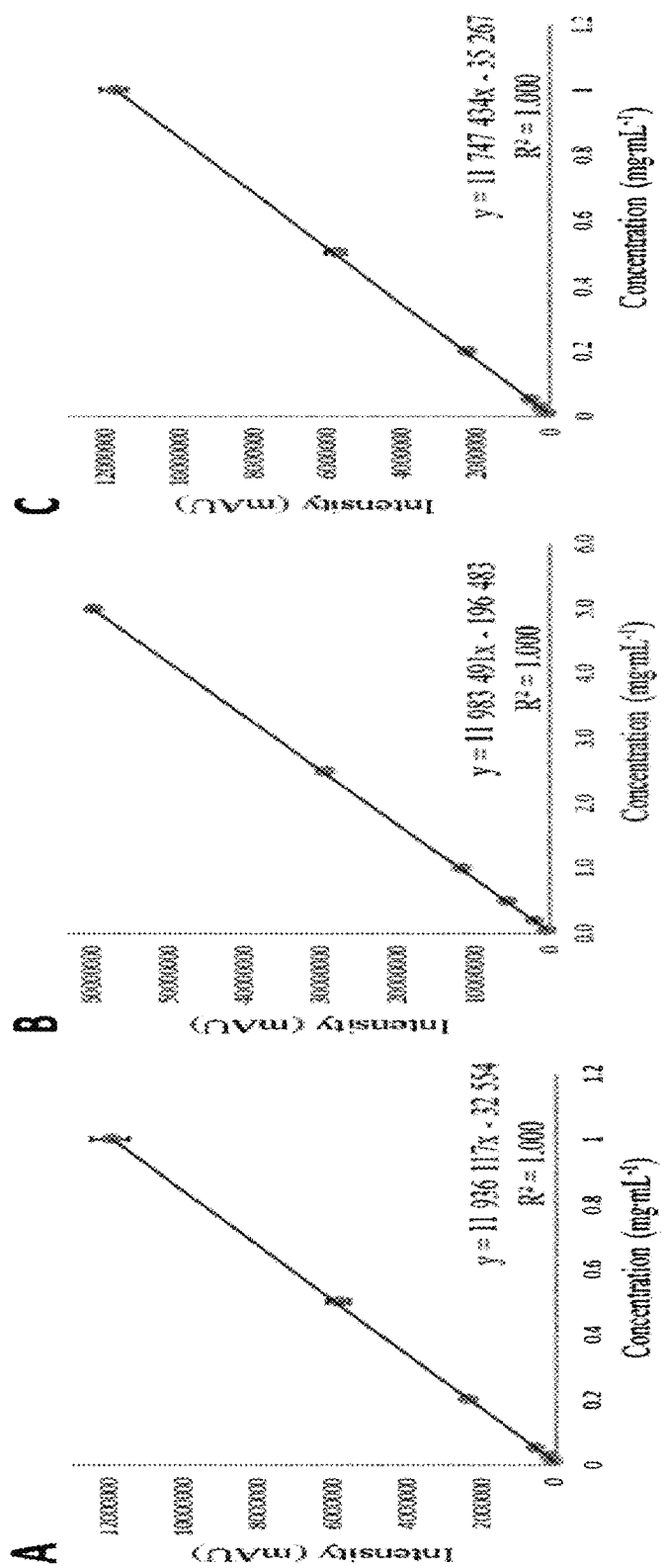
FIG. 6 is a graph showing the calibration curves of reference substances of chlorogenic acid (detection 325 nm): (A) 3-caffeyolquinic acid, (B) 5-caffeyolquinic acid and (C) 4-caffeyolquinic acid. The X-axis represents concentration in g·L$^{-1}$. The Y-axis represents intensity in milli absorption units. Each plot represents an average of three independent repetitions for six concentration levels. Linear regression was performed to determine curve slop and correlation coefficient ($R^2$).

A set of calibration curves of chlorogenic acid isomers (see FIG. 6) were linear for a range of concentration from 0.05 to 5.0 g·L$^{-1}$ for 3-CQA ($R^2$=1.000) and 0.01 to 1.0 g·L$^{-1}$ for 3-, 4- and 5-CQA ($R^2$=1.000) (see FIG. 6). The limit of quantification defined as signal-to-noise ratio>10 was 2.2 mg·µL$^{-1}$, 5.0 mg·L$^{-1}$, 3.0 mg·µL$^{-1}$ for 3-, 4- and 5-CQA, respectively.

The content of chlorogenic acid isomers in powder in relation to one gram of protein on dry matter base is calculated as follows:

$$C_{CQA}/\text{Protein}/DM \ (\%) = \left(\frac{C_{CQA}}{C_{pow} \times \frac{\text{Protein}/DM}{100}}\right) \times 100$$

wherein:

$C_{CQA}$—concentration of chlorogenic acid isomer in a sample (g·L$^{-1}$), $C_{pow}$—concentration of powder in prepared solution (g·L$^{-1}$), Protein/DM—purity of protein powder on dry matter base (%).

Colour Measurement 50 mg of protein powder are weighted, dissolved in 0.01 mol·L$^{-1}$ NaOH at a concentration of 1% (w/v) and then, the mixture is filtered on a 0.22 µm filter. The colour is recorded in CieL*a*b* scale using Lovibond PFX195 Tintometer at room temperature. To do this, a baseline calibration is performed on empty quartz cuvette. Subsequently, about 3 mL of sample is placed in cell and the colour is measured in ten replicates. From the results average values of L*, a*, b* parameters and standard deviation were determined. Additionally, the difference of colour between samples expressed by delta E (ΔE) was calculated using the following equation:

$$\Delta E = \sqrt{(L^*_{sample} - L^*_{standard}) + (a^*_{sample} - a^*_{standard}) + (b^*_{sample} - b^*_{standard})}$$

(as described in Salgado et al., LWT—Food Science and Technology 45 (2012) 65-72)

As a standard the sample of Example 1 was used.

Example 1: A Sunflower Protein Isolate from an Industrial Meal

Except if otherwise stated, percentages are mass (i.e. mass/total mass percentages).

A sunflower Isolate (SFI) according to the invention was obtained using a process comprising two main steps: 1) a neutral extraction step and 2) a purification step using ultrafiltration. For this purpose, a dehulled industrial sunflower meal, de-oiled with hexane, was used (see Table 1).

TABLE 1

Starting composition of the
sunflower seed industrial meal.

| | |
|---|---|
| DM (%) | 91.2 |
| Proteins/DM (%) | 36.8 |
| Phytic acid/Protein (%) | 13.7 |
| Lipids/DM (%) | n.d. |

DM = Dry Matter content.

The industrial sunflower defatted meal was first milled and sieved (pores 500 µm).

Solid/Liquid Extraction: 200 g of the powder thus obtained was mixed with a solution of NaCl (1.0 mol·L$^{-1}$) in a solid/liquid ratio of 1:9 (wt %). The pH was adjusted to 7.0 using a solution of NaOH (1.0 mol·L$^{-1}$). The mixture was stirred at 800 rpm at 20° C. during 30 min. After a centrifugation conducted at 15,000 g during 30 min at 20° C., the supernatant was filtered using a Whatman filter paper (Fisherbrand, cellulose, diameter 190 mm, thickness 0.17 mm, particles retention 17-30 µm). The liquid phase was collected to be purified.

Membrane purification: The ultrafiltration step was carried out using a UF system (GE Healthcare, 3 kDa cut-off hollow fiber cartridge—4 800 cm$^2$) at room temperature. The liquid phase collected at the extraction stage was washed with 6 diafiltrations volumes of aqueous solution of NaCl (0.5 mol·L$^{-1}$). Subsequently, the pH of the retentate was adjusted to 9 using an aqueous solution of NaOH (1 mol·L$^{-1}$) and then washed with 4 diafiltrations volumes with Ultrapure water. The final UF retentate was then collected and freeze dried. The color of the powder was light beige (FIG. 1).

TABLE 2

Composition of sunflower protein isolate.

| | |
|---|---|
| DM (%) | 93.5 |
| Proteins/DM (%) | 99.9 |
| $C_{3-CQA}$/Protein (%) | <0.20 (peak not detected) |
| $C_{4-CQA}$/Protein (%) | <0.20 (peak not detected) |
| $C_{5-CQA}$/Protein (%) | <0.20 (0.056)* |
| Phytic acid/Protein (%) | 1.35 |

*outside calibration range.
DM = dry matter content.

The purity (proteins on dry matter) of the powder was high (99.9%) and the phytic acid content: 1.35% on proteins (Table 2) was relatively low. The protein solubility at pH 7 and 3 was 76.8% and 89.6%, respectively.

| pH | Protein solubility of the isolate (%) |
|---|---|
| 7 | 76.8 |
| 4 | 40.8 |
| 3.5 | 79.3 |
| 3 | 89.6 |

Example 2: A Sunflower Protein Isolate from a Sunflower Cold Press Meal

The production of Sunflower Isolates (SFI) from a dehulled sunflower—cold press meal (Table 3) was conducted at low (1) or high (2) temperature. Both processes comprise three main steps: 1) an acidic washing to remove contaminates (phenolic and phytic acids as well as and other water-soluble molecules) followed by 2) a neutral extraction and 3) a membrane purification.

TABLE 3

Composition of the sunflower cold press
meal used in both examples.

| | |
|---|---|
| DM (%) | 89.3 |
| Proteins/DM (%) | 42.8 |
| Phytic acid/Protein (%) | 24.8 |
| Lipids/DM (%) | 14.6 |

1. Low-Temperature Production of Sunflower Isolate

Washing Steps 500 g of sunflower cold press meal were mixed with water at 20° C. according to a solid/liquid ratio 1:9 (wt %) and the mixture stirred at 600 rpm during 10 min. The pH was adjusted to 6.0 using an aqueous solution of citric acid (1 mol·L$^{-1}$). Then, the mixture was centrifuged at 4,000 g during 10 min at 20° C. and the supernatant was disposed of. The pellet was rewashed with water (20° C.) in a solid/liquid ratio 1:1.5 (wt %) during 5 min. After re-centrifugation at 4,000 g during 10 min at 20° C., the pellet was collected and stored at 4° C. overnight.

Solid/Liquid Extraction

The collected pellet from the previous steps was mixed with an aqueous solution of NaCl (0.5 mol·L$^{-1}$) according to a solid/liquid ratio 1:9 (wt %) and stirred at 600 rpm at 20° C. during 30 min. The pH was adjusted to 7.3 using an aqueous solution of NaOH (1 mol·L$^{-1}$). Then, the mixture was centrifuged at 4,000 g during 10 min at 20° C. After centrifugation, the supernatant was additionally filtered with a Whatman filter paper and the liquid phase was collected. The pellet from centrifugation step was rewashed with water (20° C.) in a solid/liquid ratio 1:1.5 (wt %) during 5 min and then re-centrifuged and filtered in the same way. The collected supernatants were pooled and stored at ambient temperature until microfiltration step.

Membrane Purification

A microfiltration (MF) step was carried out using a MF system (Millipore, 0.22 µm cut-off Pellicon XL Durapore PVDF membrane—0.1 m$^2$). The collected liquid phases from previous step were concentrated by a volumetric reduction factor (VRF) factor of 2 and the retentate was washed with 1 diafiltration volume of a NaCl solution of 0.5 mol·L$^{-1}$. The total microfiltration permeates were pooled and stored at ambient temperature until ultrafiltration step.

The ultrafiltration (UF) step was carried out using a UF system (GE Healthcare, 3 kDa cut-off hollow fiber cartridge—4,800 cm$^2$) at room temperature. The collected permeates from previous step were concentrated by a VRF of 2 and the retentate was washed with 5 diafiltrations volumes of water at 0.5 mol·L$^{-1}$ NaCl. Then, the pH of retentate was adjusted to 9.5 using the solution of 1 mol·L$^{-1}$ NaOH and the retentate was concentrated by a VRF of 2. Then, the retentate was washed with 3 diafiltrations volume of ultrapure water.

Figure 2:
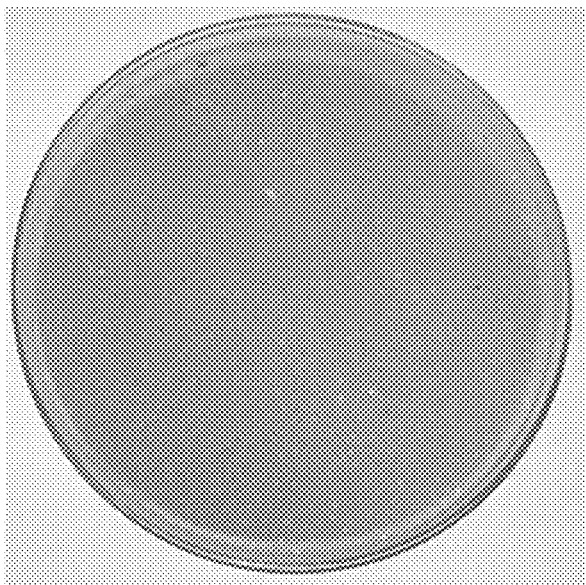
FIG. 2 is a view of a Petri dish containing a sunflower seed protein isolate according to example 2 at low temperature (20° C.).

The final UF retentate was collected and freeze dried. The color of the powder was light greenish (FIG. 2).

TABLE 4

Composition of sunflower protein isolate.

| | |
|---|---|
| DM (%) | 92.8 |
| Proteins/DM (%) | 103.4 |
| $C_{3-CQA}$/Protein (%) | <0.20 (peak not detected) |

TABLE 4-continued

Composition of sunflower protein isolate.

| | |
|---|---|
| $C_{4\text{-}CQA}$/Protein (%) | <0.20 (peak not detected) |
| $C_{5\text{-}CQA}$/Protein (%) | <0.20 (0.013)* |
| Phytic acid/Protein (%) | 0.80 |

*outside the calibration range

The purity (proteins on dry matter) of the powder was high (103.4%) and the phytic acid content: 0.8% on proteins (Table 4) was low. The protein solubility at pH 7 and 3 was 29.5% and 101.1%, respectively.

| pH | Protein solubility of the isolate (%) |
|---|---|
| 7 | 29.5 |
| 4 | 95.7 |
| 3.5 | 99.0 |
| 3 | 101.1 |

2. High-Temperature Production of Sunflower Isolate
Washing Steps 500 g of a sunflower cold press meal were mixed with water in a solid/liquid ratio 1:9 (wt %) and stirred at 600 rpm at 55° C. during 30 min. The pH of the resulting mix was measured. The pH value was not superior to 7.3, and no pH adjustment was made. Then, the mixture was centrifuged at 4,000 g during 10 min at 40° C. and filtered by sieve filtration (screen having a mesh of 150 μm). A first liquid phase was obtained. The resulting solid was rewashed with hot water (55° C.) in a solid/liquid ratio 1:1.5 (wt %) during 5 min. After re-centrifugation at 4,000 g during 10 min at 40° C. and sieve filtration (mesh of 150 μm), the collected solid constitutes the starting meal for SFI production. It was stored overnight at 4° C. The liquid phases collected from the above washing and rewashing steps were pooled and stored at 55° C. in the oven to be analysed/quantified.

Solid/Liquid Extraction

The washed pellet from the previous step was mixed with an aqueous solution of NaCl (0.3 mol·L$^{-1}$) in a solid/liquid ratio 1:9 (wt %) and stirred at 600 rpm at 55° C. during 30 min. The pH was adjusted to 7.3 using an aqueous solution of NaOH (1 mol·L$^{-1}$). Then, the mixture was centrifuged at 4,000 g during 10 min at 40° C. and filtered by sieve filtration (mesh of 150 μm). The liquid phase was collected and maintained at 55° C. in an oven. The solid collected was rewashed with hot water (55° C.) in a solid/liquid ratio 1:1.5 (wt %) during 5 min. Then it was centrifuged again at 4,000 g during 10 min at 40° C. and filtered by sieve filtration. The liquid phase from this second extraction was pooled with the previous one and stored at 55° C. in the oven until subsequent microfiltration step.

Membrane Purification

The liquid phases collected from the extraction steps are then microfiltered.

The microfiltration step was carried out using a MF system (Millipore, 0.22 μm cut-off Pellicon XL Durapore PVDF membrane 0.1 m$^2$). The pooled liquid phases from the extraction step were concentrated by a VRF of 3.5 and the retentate was washed with 2 diafiltrations volumes of hot water at 55° C. The total microfiltration permeates were pooled and stored at 55° C. in the oven until the ultrafiltration step. The ultrafiltration step was carried out using a UF system (GE Healthcare, 3 kDa cut-off hollow fiber cartridge 4,800 cm$^2$). The pooled permeates from the microfiltration step were concentrated by a VRF of 4 and the retentate was washed with 5 diafiltrations volumes of a hot aqueous solution of NaCl (0.2 mol·L$^{-1}$) at 55° C. The pH of retentate was subsequently adjusted to 9 using an aqueous solution of NaOH (1 mol·L$^{-1}$). Then, the retentate was washed with 3 diafiltrations volume of hot water (55° C.) and concentrated by a VRF of 2.

Figure 3:
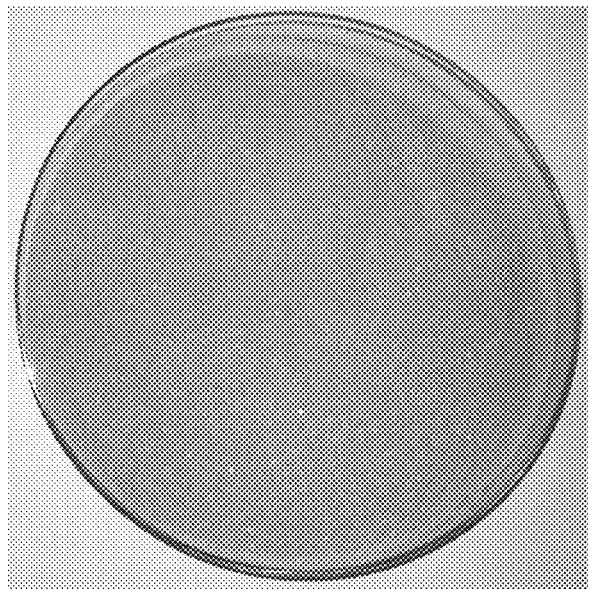
FIG. 3 is a view of a Petri dish containing a sunflower seed protein isolate according to example 2 at high temperature (55° C.).
Figure 4:
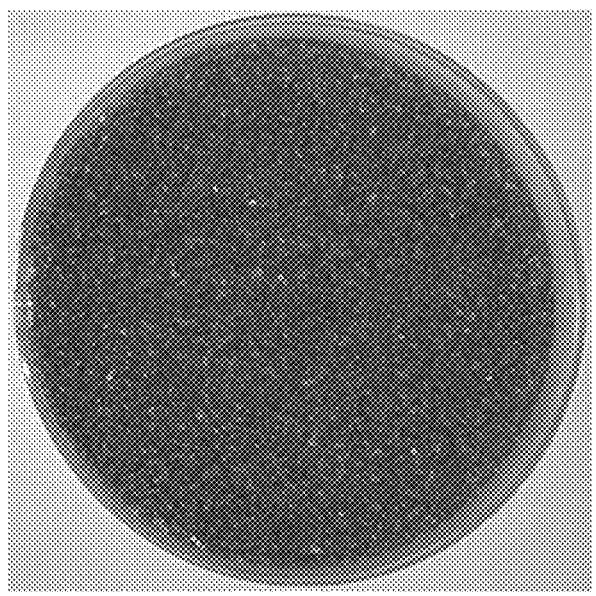
FIG. 4 is a view of a Petri dish containing a sunflower protein isolate from sunflower cold-pressed meal according to example 3.

The final UF retentate was collected and freeze dried for 72 h. The colour of the powder was beige with greenish hue (FIG. 3).

TABLE 5

Composition of sunflower protein isolate

| | |
|---|---|
| DM (%) | 92.9 |
| Proteins/DM (%) | 100.9 |
| $C_{3\text{-}CQA}$/Protein (%) | <0.20 (peak not detected) |
| $C_{4\text{-}CQA}$/Protein (%) | <0.20 (peak not detected) |
| $C_{5\text{-}CQA}$/Protein (%) | <0.20 (0.010)* |
| Phytic acid/Protein (%) | 0.78 |

*outside the calibration range

The purity (proteins on dry matter) of the powder was high (100.9%) and the phytic acid content 0.78% on proteins (Table 5) was low. The protein solubility at pH 7 and 3 was 99.8% and 101.2%, respectively.

| pH | Protein solubility of the isolate (%) |
|---|---|
| 7 | 99.8 |
| 4 | 36.9 |
| 3.5 | 102.8 |
| 3 | 101.2 |

Example 3: Detoxified Sunflower Isolates from Sunflower Cold Press Meal

Detoxified Sunflower Isolate (DSFI) was produced from a cold press meal of dehulled sunflower seed (Table 6) at a pilot scale by using three main steps: 1) an acidic wash to remove contaminates (such as phenolic compounds and phytic acid) and other water soluble molecules, followed by 2) a neutral extraction and 3) a membrane purification in order to obtain a DSFI.

TABLE 6

Starting composition of the cold press meal of dehulled sunflower seed.

| | |
|---|---|
| DM (%) | 89.3 |
| Proteins/DM (%) | 42.8 |
| Phytic acid/Protein (%) | 24.8 |
| Lipids/DM (%) | 14.6 |

Acidic Washing Steps 60 kg of a sunflower cold press meal were washed by mixing with some acidic water (pH 2) in a ratio meal:water of 1:8 (wt %) at 55° C. in order to form a slurry having a pH of 4.8±0.2. The slurry was agitated at 160 rpm during 15 min and decanted with a decanter centrifuge at 4,600 g (Z23, FlottWeg). The decanted sludge was rewashed by mixing it again with some acidic water at pH 4.8±0.2, at a temperature of 55° C., in a ratio sludge:water of 1:3.5 (wt %) to form a new slurry having a pH of 4.8±0.2. The slurry formed was agitated at 160 rpm during 15 min and decanted with a decanter centrifuge at 4,600 g (Z23, FlottWeg). The sludge from the rewash constitutes the starting meal for DSFI production.

Extraction

For DSFI production, the rewashed sludges from the second acidic wash were mixed with water in a ratio sludge:water of 1:3.5 (wt %) at 55° C. under agitation at 160 rpm during 30 min. The pH was adjusted to 7.3 by using aqueous solutions of phosphoric acid or NaOH (both at 1 mol·L$^{-1}$).

The slurry was decanted with a decanter centrifuge at 4,600 g (Z23, FlottWeg) at room temperature. The decanted liquid phase was reheated at 55° C. and clarified with a disk stack clarifier at 17,000 g (EasyScale, GEA), in order to remove fines, and skimmed with a 3-phases disk stack skimmer (ASE40, GEA) at 55° C. in order to remove the oil (at least partially).

Purification

Microfiltration

The (partially) skimmed liquid phase (heavy phase) was microfiltered using a MF system (Pall, 0.1 μm cutoff ceramic GP membrane—0.7 m$^2$).

Ultrafiltration

The heavy phase was concentrated 7.2 times and the retentate was diafiltered with 2 diafiltration volumes with hot water at 55° C. with UF system (Koch, 5 kDa cutoff PES membrane—4.3 m$^2$)

The total microfiltration and diafiltration (MF+DF) permeates were pooled and ultrafiltered with a UF system (Koch, 5 kDa cutoff PES membrane—4.3 m$^2$). The MF+DF permeates was concentrated 4.5 times at room temperature.

The UF retentate was diafiltered with 2 diavolumes of salted water NaCl (0.4 mol·L$^{-1}$) following by 4 diafiltrations volumes of water at 20° C. The final UF retentate was freeze dried. The colour of the powder was medium greenish brown.

TABLE 7

Composition of sunflower protein isolate.

| | |
|---|---|
| DM (%) | 98.1 |
| Proteins/DM (%) | 97.4 |
| $C_{3-CQA}$/Protein(%) | <0.20 (peak not detected) |
| $C_{4-CQA}$/Protein (%) | <0.20 (peak not detected) |
| $C_{5-CQA}$/Protein(%) | <0.20 (0.029)* |
| Phytic acid/Protein(%) | 3.38 |

*outside the calibration range

The purity (proteins on dry matter) of the powder was high (97.4%) as well as the phytic acid content: 3.38% on proteins (Table 7). The protein solubility at pH 7 and 3 was 100.1% and 67.3%, respectively.

| pH | Protein solubility of the isolate (%) |
|---|---|
| 7 | 100.1 |
| 4 | 32.0 |
| 3.5 | 36.9 |
| 3 | 67.3 |

Colour Measurement

As can be shown from the figures, the isolate present a light coloration, which is high in demand in the food industry. The L*, a*, b* parameters of these isolates are as listed in Table 8 below:

| Example | L* | a* | b* | AE |
|---|---|---|---|---|
| 1 | 84.32 ± 3.71 | 1.08 ± 1.45 | 34.78 ± 2.66 | — |
| 2.1 | 84.39 ± 4.87 | 0.23 ± 0.88 | 41.30 ± 2.74 | 6.58 |
| 2.2 | 81.05 ± 4.87 | 0.22 ± 0.94 | 24.11 ± 1.39 | 11.20 |
| 3 | 39.62 ± 3.74 | 10.08 ± 1.80 | 49.78 ± 3.32 | 48.01 |

Example 4: Solubility of the Protein Isolates of Previous Example at pH 3, 3.5, 4 and 7 at a Specific Ionic Strength (30 nM) at Room Temperature (about 20° C.)

Additional protein solubility measurements were performed with the protein isolates obtained according to examples 1, 2.1, 2.2 and 3 above. In non-controlled conditions of temperature of about 20° C., each of these proteins were dispersed to final concentration of 4.0 mg/mL in water and the pH adjusted to 8.5 by addition of small amounts of NaOH solutions.

The ionic strength was adjusted to 0.03 mol·L$^{-1}$ by adding NaCl. The pH of the protein solutions was lowered by adding various amounts of HCl or NaOH solutions (0.01 mol·L$^{-1}$) to obtain final pH at 3.0, 3.5, 4 or 7, and kept constantly (±0.05) during 2 h under agitation (100 rpm) at room temperature. Next, the samples were centrifuged for 15 min at 12100×g at 20° C.

The protein concentration in supernatant was measured by the Kjeldahl method (AOAC method 991.20, 1995). Solubility was expressed as proportion (%) of the amount of protein dissolved at pH 8.5.

The change of centrifugation speed and of measurement of protein concentration when compared to the one disclosed in Gonzalez-Perez et al. 2005 are on consequential. The solubility data are ratio of protein concentration (hence independent from the method) and a centrifugation speed of 12,100 g provides equivalent results to remove solid particulates when compared to a speed of 15,800 g.

The results of these measurements are compiled in table 9 below which includes the solubility data of Sunflower isolate obtained using methanol extraction in order to dephenolized the isolate as described in in FIG. 2, table a) of Gonzalez-Perez et al. 2005 (*Physicochemical properties of 2S albumins and the corresponding protein isolate from sunflower (Helianthus annuus)*) in JFS C: Food Chemistry and toxicology Vol. 70, Nr. 1, 2005.

TABLE 9

| | Protein solubility (%) | | | |
|---|---|---|---|---|
| Isolate tested | pH 3 | pH 3.5 | pH 4.0 | pH 7 |
| Example 1 | 83.98 | / | / | 67.22 |
| Example 2.1 | 96.90 | 100.72 | 91.00 | 43.90 |
| Example 2.2 | 97.00 | 93.74 | 35.74 | 95.97 |
| Example 3 | 60.63 | 42.29 | 30.04 | 94.75 |
| Gonzalez-Perez et al. 2005 | about 90% | about 80 % | about 40% | about 60% |

Example 5: Analysis of the Isolate of the Invention Obtained in Examples 1, 2.1 and 2.2

SE-HPLC analysis was performed according to the method of Defaix et al. (2019). The analyses were carried out on a HPLC Shimadzu LC30 system coupled with photodiode array detector (PDA) and operated by LabSolutions software, all from Shimadzu Corporation (Kyoto, Japan). The solutions of proteins were prepared at a concentration of 5 g·L$^{-1}$ in 0.25 mol·L$^{-1}$ Tris-HCl buffer, pH 7/0.5 mol·L$^{-1}$ NaCl (v/v).

5-20 μL of sample was injected into a Biosep SEC s-2000 column (300×7.8 mm; 5 μm) from Phenomenex (Torrance, CA, USA). The exclusion range of molecular weight was between 1 and 300 kDa. During analysis the autosampler and column compartment were maintained at 20 and at 35° C., respectively. The mobile phase consisted of acetonitrile/water/trifluoracetic acid (45:54.9:0.1 v/v). The elution flow rate was set at 0.6 mL·min$^{-1}$. All solvents were HPLC grade and were supplied from Fisher Scientific (Hampton, USA). The ultrapure water (H$_2$O) with resistivity≥18.2 MQ·cm$^{-1}$ was used. The PDA signal was recorded between 190 and 400 nm with maximal absorption at 214 nm for protein detection. Assuming the same value of molar extinction coefficient for sunflower globulins and albumins as it was previously demonstrated by Defaix et al. (2019), the content of globulins (C$_{GLOB}$) and albumins (C$_{ALB}$) in relation to total sunflower proteins, that is the total amount of globulins and albumins in the extract (as other amounts of other proteins are considered negligible) were calculated as follow:

$$C_{GLOB} = \frac{A_{GLOB}}{A_{GLOB} + A_{ALB}} \times 100 \quad \text{(Equation. 1)}$$

$$C_{ALB} = \frac{A_{ALB}}{A_{GLOB} + A_{ALB}} \times 100 \quad \text{(Equation. 2)}$$

where A$_{GLOB}$ and A$_{ALB}$ is peak surface at 214 nm corresponding to globulins or albumins, respectively. All measurements were performed in triplicate and a mean value was calculated. The results are shown in Table 10.

TABLE 10

| Example | Globulins (wt %) | Albumins (wt %) |
|---------|------------------|-----------------|
| 1       | 76.50 ± 2.30     | 23.50 ± 2.30    |
| 2.1     | 71.80 ± 0.93     | 28.20 ± 0.93    |

The invention claimed is:

1. A process for preparing a sunflower protein isolate, said process comprising the following steps:
    (a) providing an at least partially defatted seed meal, said seed meal being a sunflower seed meal and having a proportion of dry matter ranging from 80 wt % to 98 wt %;
    (b) mixing said at least partially defatted seed meal with an aqueous NaCl solution at a pH of about 6 to 8, in order to solubilize proteins present in said at least partially defatted seed meal and to thus obtain a solubilized protein solution, wherein said aqueous NaCl solution has a NaCl concentration ranging from 0 to 1.2 mol·L$^{-1}$;
    (c) separating said solubilized protein solution from solids therein;
    (d) diafiltering said solubilized protein solution through an ultrafiltration membrane system having a molecular weight cutoff of 1 to 100 kDa, said diafiltering step being effected using:
        an aqueous NaCl diafiltration solution having a NaCl concentration ranging from 0.1 to 0.6 mol·L$^{-1}$; and
        at least 2 diavolumes of said aqueous NaCl diafiltration solution, to obtain a NaCl-diafiltered protein solution;
    (e) subsequently to step (d), diafiltering said NaCl-diafiltered protein solution through an ultrafiltration membrane system with a molecular weight cutoff of 1 to 100 kDa, using water, to obtain a purified protein solution;
    (f) concentrating said purified protein solution to obtain a purified protein concentrate; and
    (g) drying said purified protein concentrate to obtain said protein isolate;
    wherein said process does not contain a step of precipitation of said protein prior to the step (d).

2. The process of claim 1, wherein said aqueous NaCl solution of step (b) has a NaCl concentration ranging from 0.3 to 0.5 mol·L$^{-1}$.

3. The process of claim 1, wherein said diafiltering step of step (d) is carried out using at least 3 to up to about 30 diavolumes of said aqueous NaCl diafiltration solution.

4. The process of claim 1, wherein prior to step b) a washing step wherein said at least partially defatted seed meal is washed with water thus producing a washing mix.

5. The process of claim 4, wherein the pH of said washing mix is adjusted to range from 4 to 6.

6. The process of claim 1, wherein all of the steps are carried out at a temperature ranging from 50° C. to 60° C.

7. The process of claim 1, wherein the pH of the NaCl diafiltered solution of step d) is adjusted to a pH ranging from 7 to 10 before being subjected to step (e).

8. The process of claim 1, wherein prior to step d) the solubilized protein solution is microfiltrated through a filtration membrane having a nominal pore size ranging from 0.1 to 1 μm and retentate collected is the solubilized protein solution submitted to step d).

9. The process of claim 1, wherein during step f) said purified protein solution is concentrated by a volumetric reduction factor of 2 or more.

10. The process of claim 1, wherein said drying step (g) is freeze drying.

11. The process of claim 1, wherein said diafiltering step of step (d) is carried out using at least 5 to up to about 30 diavolumes of said aqueous NaCl diafiltration solution.

12. The process of claim 1, wherein during step f) said purified protein solution is concentrated by a volumetric reduction factor of 4.

* * * * *